United States Patent
Goshayeshgar

(10) Patent No.: US 9,402,648 B2
(45) Date of Patent: Aug. 2, 2016

(54) RETRACTABLE DEVICE TO DISSECT AND EVACUATE LIGAMENTUM FLAVUM IN LUMBAR SPINAL STENOSIS

(71) Applicant: KYPHON SARL, Neuchatel (CH)

(72) Inventor: Mojan Goshayeshgar, Atherton, CA (US)

(73) Assignee: KYPHON SÀRL, Neuchâtel (CH)

( * ) Notice: Subject to any disclaimer, the term of this patent is extended or adjusted under 35 U.S.C. 154(b) by 540 days.

(21) Appl. No.: 13/834,922

(22) Filed: Mar. 15, 2013

(65) Prior Publication Data

US 2014/0277038 A1    Sep. 18, 2014

(51) Int. Cl.
| | |
|---|---|
| A61B 17/3205 | (2006.01) |
| A61B 17/32 | (2006.01) |
| A61B 17/00 | (2006.01) |
| A61B 18/14 | (2006.01) |
| A61B 18/00 | (2006.01) |

(52) U.S. Cl.
CPC ..... *A61B 17/3205* (2013.01); *A61B 17/320016* (2013.01); *A61B 18/148* (2013.01); *A61B 2017/00349* (2013.01); *A61B 2017/320064* (2013.01); *A61B 2018/00601* (2013.01); *A61B 2018/1415* (2013.01); *A61B 2018/1422* (2013.01); *A61B 2217/005* (2013.01); *A61B 2217/007* (2013.01)

(58) Field of Classification Search
CPC ........... A61B 17/32; A61B 17/320016; A61B 17/3205; A61B 17/3207; A61B 17/32075; A61B 17/3421; A61B 2017/00349; A61B 2017/320733; A61B 2018/00601
See application file for complete search history.

(56) References Cited

U.S. PATENT DOCUMENTS

| | | | | |
|---|---|---|---|---|
| 3,628,524 A * | 12/1971 | Jamshidi | ............... | A61B 10/025 600/567 |
| 3,877,434 A * | 4/1975 | Ferguson | ........... | A61B 17/0485 251/7 |
| 3,929,123 A * | 12/1975 | Jamshidi | ............ | A61B 10/0275 600/567 |
| 4,991,600 A * | 2/1991 | Taylor | ................ | A61B 10/0275 600/567 |
| 5,053,041 A * | 10/1991 | Ansari | ................... | A61B 17/29 606/1 |
| 5,366,476 A * | 11/1994 | Noda | ................. | A61B 17/2909 606/206 |
| 5,376,096 A * | 12/1994 | Foster | ................ | A61B 17/0469 606/147 |
| 5,385,570 A * | 1/1995 | Chin | .................. | A61B 17/1611 600/564 |
| 5,397,333 A * | 3/1995 | Knoepfler | ...... | A61B 17/320016 606/167 |
| 5,499,991 A * | 3/1996 | Garman | ............. | A61B 17/0483 606/148 |

(Continued)

*Primary Examiner* — Ryan J Severson
(74) *Attorney, Agent, or Firm* — Martin & Ferraro LLP

(57) ABSTRACT

A cutting device for performing a surgical procedure includes an elongated shaft extending between a proximal end and a distal end, a first cutting element, and a second cutting element. The elongated shaft of the cutting device includes an inner surface defining a passageway. The first cutting element extends from the distal end of the elongated shaft so as to contact tissue. The second cutting element is disposed at least partially within the passageway and extends from the distal end of the elongated shaft. The second cutting element is configured for retractable extension beyond the distal end of the elongated shaft so as to contact tissue. The cutting device also includes a deployment mechanism disposed with the proximal end of the elongated shaft for engaging and actuating the second element.

17 Claims, 4 Drawing Sheets

(56) References Cited

U.S. PATENT DOCUMENTS

| | | | | |
|---|---|---|---|---|
| 5,512,037 A * | 4/1996 | Russell | A61B 17/0218 | 600/201 |
| 5,573,008 A * | 11/1996 | Robinson | A61B 10/0266 | 600/567 |
| 5,578,030 A * | 11/1996 | Levin | A61B 10/0233 | 606/39 |
| 5,582,618 A * | 12/1996 | Chin | A61B 17/1611 | 606/170 |
| 5,655,542 A * | 8/1997 | Weilandt | A61B 10/0266 | 600/567 |
| 5,758,665 A * | 6/1998 | Suval | A61B 17/00008 | 128/898 |
| 5,792,168 A * | 8/1998 | Suval | A61B 17/00008 | 30/136 |
| 5,810,744 A * | 9/1998 | Chu | A61B 10/0275 | 600/567 |
| 5,823,971 A * | 10/1998 | Robinson | A61B 10/0266 | 600/567 |
| 5,910,121 A * | 6/1999 | Paolo | A61B 10/025 | 600/562 |
| 5,957,919 A * | 9/1999 | Laufer | A61B 18/1492 | 606/27 |
| 6,027,458 A * | 2/2000 | Janssens | A61B 10/0275 | 600/567 |
| 6,030,400 A * | 2/2000 | Johnson | A61B 10/0233 | 606/167 |
| 6,214,010 B1 * | 4/2001 | Farley | A61B 17/1611 | 606/83 |
| 6,419,684 B1 * | 7/2002 | Heisler | A61B 17/32002 | 600/567 |
| 6,527,771 B1 * | 3/2003 | Weadock | A61B 17/00008 | 606/170 |
| 6,572,563 B2 * | 6/2003 | Ouchi | A61B 10/0275 | 600/564 |
| 6,676,673 B2 * | 1/2004 | Chang | A61B 17/06109 | 606/139 |
| 6,733,496 B2 * | 5/2004 | Sharkey | A61B 18/1492 | 128/898 |
| 7,137,956 B2 * | 11/2006 | Nishtalas | A61B 10/0266 | 600/567 |
| 7,308,896 B2 * | 12/2007 | Cruz | A61B 17/3211 | 128/207.29 |
| 7,455,675 B2 * | 11/2008 | Schur | A61B 17/00008 | 606/139 |
| 7,553,307 B2 * | 6/2009 | Bleich | A61B 17/1659 | 606/1 |
| 7,651,503 B1 * | 1/2010 | Coe | A61B 17/320016 | 606/108 |
| 7,896,879 B2 * | 3/2011 | Solsberg | A61B 10/0275 | 606/79 |
| 8,034,070 B2 * | 10/2011 | Tal | A61B 17/00008 | 128/898 |
| 8,394,102 B2 * | 3/2013 | Garabedian | A61B 17/00234 | 606/279 |
| 8,608,767 B2 * | 12/2013 | Tal | A61B 17/00008 | 30/136 |
| 8,834,500 B2 * | 9/2014 | Mustapha | A61B 17/00008 | 606/159 |
| 8,920,442 B2 * | 12/2014 | Sibbitt, Jr. | A61B 17/10 | 606/139 |
| 2001/0005778 A1 * | 6/2001 | Ouchi | A61B 10/0275 | 600/564 |
| 2003/0036767 A1 * | 2/2003 | Chang | A61B 17/06109 | 606/148 |
| 2003/0125759 A1 * | 7/2003 | Mirizzi | A61B 17/00008 | 606/159 |
| 2004/0087967 A1 * | 5/2004 | Schur | A61B 17/00008 | 606/108 |
| 2004/0133208 A1 * | 7/2004 | Weikel | A61B 17/1671 | 606/79 |
| 2005/0080441 A1 * | 4/2005 | Dodge | A61F 9/00763 | 606/171 |
| 2005/0216048 A1 * | 9/2005 | Suval | A61B 17/00008 | 606/194 |
| 2005/0234481 A1 * | 10/2005 | Waller | A61B 17/0467 | 606/148 |
| 2005/0279363 A1 * | 12/2005 | Cruz | A61B 17/3211 | 128/207.29 |
| 2006/0030785 A1 * | 2/2006 | Field | A61B 10/02 | 600/567 |
| 2006/0089609 A1 * | 4/2006 | Bleich | A61B 17/1659 | 604/272 |
| 2006/0089633 A1 * | 4/2006 | Bleich | A61B 17/1659 | 606/32 |
| 2006/0089640 A1 * | 4/2006 | Bleich | A61B 17/1659 | 606/45 |
| 2006/0094976 A1 * | 5/2006 | Bleich | A61B 17/1659 | 600/547 |
| 2006/0095028 A1 * | 5/2006 | Bleich | A61B 17/1659 | 606/39 |
| 2006/0095059 A1 * | 5/2006 | Bleich | A61B 17/1659 | 606/170 |
| 2006/0100651 A1 * | 5/2006 | Bleich | A61B 17/1659 | 606/167 |
| 2006/0122458 A1 * | 6/2006 | Bleich | A61B 17/1659 | 600/101 |
| 2006/0122535 A1 * | 6/2006 | Daum | A61B 10/02 | 600/565 |
| 2006/0135882 A1 * | 6/2006 | Bleich | A61B 17/1659 | 600/546 |
| 2007/0049968 A1 * | 3/2007 | Sibbitt | A61B 17/10 | 606/213 |
| 2007/0055263 A1 * | 3/2007 | Way | A61B 17/1671 | 606/82 |
| 2007/0123890 A1 * | 5/2007 | Way | A61B 17/320016 | 606/79 |
| 2007/0162061 A1 * | 7/2007 | Way | A61B 17/1611 | 606/167 |
| 2008/0071304 A1 * | 3/2008 | Tal | A61B 17/00008 | 606/190 |
| 2008/0221383 A1 * | 9/2008 | Way | A61B 17/295 | 600/3 |
| 2009/0259234 A1 * | 10/2009 | Waller | A61B 17/0467 | 606/148 |
| 2010/0030247 A1 * | 2/2010 | Pikus | A61B 17/00008 | 606/159 |
| 2010/0089405 A1 * | 4/2010 | Johnson | A61B 17/3211 | 128/207.29 |
| 2011/0009705 A1 * | 1/2011 | Bombard | A61B 17/02 | 600/210 |
| 2011/0264124 A1 * | 10/2011 | Boyle | A61B 17/00008 | 606/159 |
| 2011/0301624 A1 * | 12/2011 | Tal | A61B 17/00008 | 606/159 |
| 2012/0226297 A1 * | 9/2012 | Mustapha | A61B 17/00008 | 606/159 |
| 2012/0271357 A1 * | 10/2012 | Arthur | A61B 17/1604 | 606/279 |
| 2014/0276729 A1 * | 9/2014 | Goshayeshgar | A61B 17/320016 | 606/33 |
| 2014/0277038 A1 * | 9/2014 | Goshayeshgar | A61B 17/3205 | 606/170 |

* cited by examiner

RETRACTABLE DEVICE TO DISSECT AND EVACUATE LIGAMENTUM FLAVUM IN LUMBAR SPINAL STENOSIS

TECHNICAL FIELD

The present disclosure generally relates to medical devices for the treatment of hypertrophied ligamentum flavum, and more particularly to a surgical system and method employing a retractable device to dissect and evacuate tissue.

BACKGROUND

Spinal stenosis typically occurs when the spinal cord, cauda equina and/or nerve root(s) are impinged by one or more tissues in the spine, such as a buckled or thickened ligamentum flavum. Impingement of neural and/or neurovascular tissue in the spine by a buckled or thickened ligamentum flavum may cause pain, numbness and/or loss of strength or mobility in one or both of a patient's lower limbs and/or of the patient's back.

In lumbar spinal stenosis (LSS), the space around the spinal cord becomes narrow, thus compressing the spinal cord and the nerve roots. This causes back pain with neurogenic claudication, i.e., pain, numbness, or weakness in the legs that worsens with standing or walking and is alleviated with sitting or leaning forward. Compression of neural elements generally occurs as a result of hypertrophied facet or ligamentum flavum hypertrophy. LSS is one of the most common reasons for back surgery and the most common reason for lumbar spine surgery in adults over 65 years of age. Patients suffering from spinal stenosis are typically first treated with conservative approaches such as exercise therapy, analgesics, anti-inflammatory medications, and epidural steroid injections. When these conservative treatment options fail and symptoms are severe, surgery may be required to remove impinging tissue and decompress the impinged nerve tissue.

The source of most cases of lumbar spinal stenosis is thickening of the ligamentum flavum. Spinal stenosis may also be caused by subluxation, facet joint hypertrophy, osteophyte formation, underdevelopment of spinal canal, spondylosis deformans, degenerative intervertebral discs, degenerative spondylolisthesis, degenerative arthritis, ossification of the vertebral accessory ligaments and the like. A less common cause of spinal stenosis, which usually affects patients with morbid obesity or patients on oral corticosteroids, is excess fat in the epidural space. The excessive epidural fat compresses the dural sac, nerve roots and blood vessels contained therein and resulting in back and leg pain and weakness and numbness of the legs. Spinal stenosis may also affect the cervical and, less commonly, the thoracic spine.

Patients suffering from spinal stenosis are typically first treated with exercise therapy, analgesics and anti-inflammatory medications. These conservative treatment options frequently fail. If symptoms are severe, surgery is required to decompress the canal and nerve roots.

To correct stenosis in the lumbar region, an incision is made in the back and the muscles and supporting structures are stripped away from the spine, exposing the posterior aspect of the vertebral column. The thickened ligamentum flavum is then exposed by removal of the bony arch (lamina) covering the back of the spinal canal (laminectomy). The thickened ligament can then be excised with sharp dissection with a scalpel or punching instruments such as a Kerison punch that is used to remove small chips of tissue. The procedure is performed under general anesthesia. Patients are usually admitted to the hospital for approximately five to seven days depending on the age and overall condition of the patient. Patients usually require between six weeks and three months to recover from the procedure. Many patients need extended therapy at a rehabilitation facility to regain enough mobility to live independently.

Much of the pain and disability after an open laminectomy is due to the tearing and cutting of the back muscles, blood vessels and supporting ligaments and nerves that occurs during the exposure of the spinal column. Also, because these spine stabilizing back muscles and ligaments are stripped and cut off, the spine these patients frequently develop spinal instability post-operatively.

Minimally invasive techniques result in less post-operative pain and faster recovery compared to traditional open surgery. Percutaneous interventional spinal procedures can be performed with local anesthesia, thereby sparing the patient the risks and recovery time required with general anesthesia. Another advantage is that there is less damage to the paraspinal muscles and ligaments with minimally invasive techniques reducing pain and preserving these important stabilizing structures.

Various techniques for minimally invasive treatment of the spine are known. Microdiscectomy is performed by making a small incision in the skin and deep tissues to create a portal to the spine. microscope is then used to aid in the dissection of the adjacent structures prior to discectomy. The recovery for this procedure is much shorter than traditional open discectomies. Percutaneous discectomy devices with fluoroscopic guidance have been used successfully to treat disorders of the disc but not to treat spinal stenosis or the ligamentum flavum directly. Arthroscopy or direct visualization of the spinal structures using a catheter or optical system have also been proposed to treat disorders of the spine including spinal stenosis however these devices still use miniaturized standard surgical instruments and direct visualization of the spine similar to open surgical procedures. These devices and techniques are limited by the small size of the canal and these operations are difficult to perform and master. Also these procedures are painful and often require general anesthesia. The arthroscopy procedures are time consuming and the fiber optic systems are expensive to purchase and maintain. In addition, because the nerves of the spine pass through the core of the spine directly in front of the ligamentum flavum, any surgery, regardless of whether is open or percutaneous includes a risk of damage to those nerves.

It is desirable to provide a simple method and device for treating spinal stenosis and other spinal disorders without requiring open surgery. It is further desired to provide a system whereby the risk of damage to the thecal sac containing the spinal nerves can be reduced. Accordingly, there is a need for devices and methods to provide efficient severing or cutting of tissue including bone that can be used during a minimally invasive procedure and/or during an open surgical procedure, such as open decompression. Further, there is also a need for devices and methods that provide fine dissection capabilities of bone without damaging nerves.

SUMMARY

In one embodiment, in accordance with the principle so the present disclosure, a device for performing a surgical procedure includes an elongated shaft extending between a proximal end, a distal end and an inner surface defining a passageway. A first cutting element extending from the distal end of the elongated shaft so as to contact tissue. A second cutting element disposed in the passageway and extending from the distal end of the elongated shaft and configured for retractable extension beyond the distal end of the elongated shaft so as to contact tissue. A deployment mechanism disposed with the proximal end of the elongated shaft and configured to engage the second cutting element.

In one embodiment, a cutting device for performing a surgical procedure includes a cannula extending between a proximal end, a distal end and an inner surface defining a passageway. A stationary anchor hook extending from the distal end of the cannula so as to contact tissue. An orbital hook disposed in the passageway and extending from the distal end of the cannula and configured for retractable extension beyond the distal end of the cannula so as to contact tissue. A deployment mechanism disposed with the proximal end of the elongated shaft and configured to engage the second cutting element.

In one embodiment, a method for removing tissue at a surgical site comprising providing a device comprising: a cannula extending between a proximal end, a distal end and an inner surface defining a passageway; a stationary anchor hook extending from the distal end of the cannula so as to contact tissue; an orbital hook disposed in the passageway and extending from the distal end of the cannula and configured for retractable extension beyond the distal end of the cannula so as to contact tissue; and a deployment mechanism disposed with the proximal end of the elongated shaft and configured to engage the second cutting element. Creating an access path to the surgical site. Inserting the device into the surgical site such that the anchor hook pulls on a ligamentum flavum to dissect tissue. Deploying the orbital hook to evacuate tissue into the cannula.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
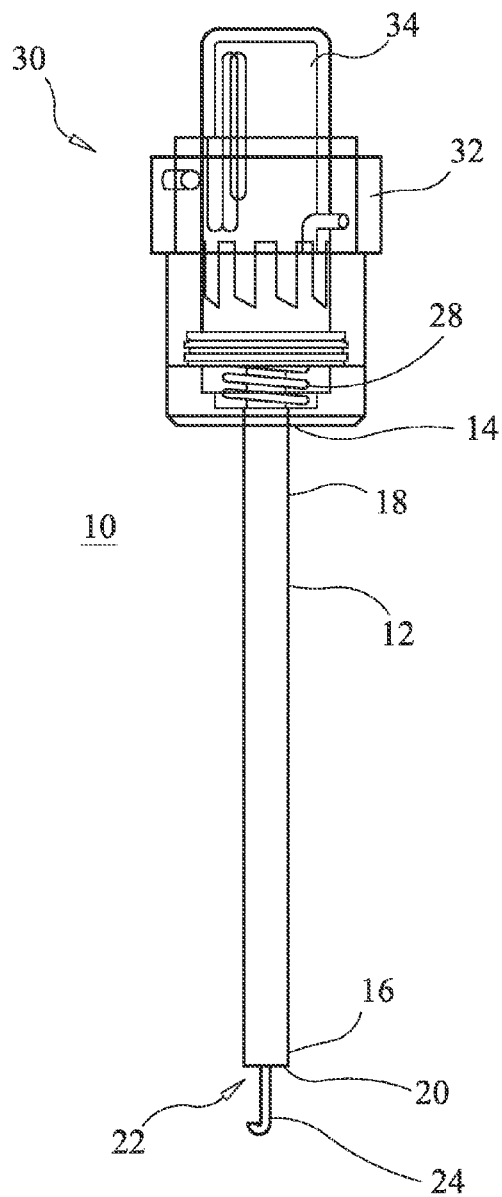
FIG. 1 is a perspective view, with partial cross section, of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system and method for nerve destruction.

Devices for efficient severing or cutting of a material or substance such as nerve and/or soft tissue suitable for use in open surgical and/or minimally invasive procedures are disclosed. The following description is presented to enable any person skilled in the art to make and use the present disclosure. Descriptions of specific embodiments and applications are provided only as examples and various modifications will be readily apparent to those skilled in the art.

Lumbar spinal stenosis (LSS) may occur from hypertrophied bone or ligamentum flavum, or from a lax ligamentum flavum that collapses into the spinal canal. LSS can present clinical symptoms such as leg pain and reduced function. Conventional treatments include epidural steroid injections, laminotomy, and laminectomy. Surgical interventions which remove at least some portion of the lamina are usually performed through a relatively large incision, and may result in spinal instability from removal of a large portion of the lamina. Consequently, a percutaneous approach which removes just enough tissue (lamina or ligamentum flavum) to be effective is provided.

In one embodiment, a retractable ballpoint pen-like mechanism to dissect and evacuate the hypertrophied ligamentum flavum in Lumbar Spinal Stenosis is provided. In one embodiment, the device includes an anchor hook. The anchor hook is a central, stationary hook to anchor and pull on ligamentum flavum to increase the "potential epidural space". In one embodiment, a suture anchor mechanism can also be utilized. The anchor hook will evacuate the dissected LF tissue into the barrel. An orbiting hook is deployed a distance not further than anchor hook The orbiting hook is deployed with a deployment mechanism similar to that of a retractable ballpoint pen-like mechanism. The atraumatic tip of the orbiting hook will pass through the ligamentum flavum. The inner cutting edge of the orbiting hook will cut through ligamentum flavum fibers when it retracts into the barrel. 6 to 20 consecutive deployments of the orbiting hook an annular dissection to the ligamentum flavum will be achieved. Upon completion of the annular cut the anchor hook will evacuate the dissected ligamentum flavum into the barrel.

It is contemplated that one or all of the components of the surgical system may be disposable, peel-pack, pre-packed sterile devices. One or all of the components of the surgical system may be reusable. The surgical system may be configured as a kit with multiple sized and configured components, such as, for example, inflatable members (balloons) that are preformed to have different sizes and shapes.

The present disclosure may also be alternatively employed with procedures for treating the muscles, ligaments, tendons or any other body part. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The components of system 10 can be fabricated from biologically acceptable materials suitable for medical applications, including metals, synthetic polymers, ceramics and bone material and/or their composites, depending on the particular application and/or preference of a medical practitioner. For example, the components of system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference.

The components of system 10, individually or collectively, may also be fabricated from a heterogeneous material such as a combination of two or more of the above-described materials. The components of system 10 may be monolithically formed, integrally connected or include fastening elements and/or instruments, as described herein.

Figure 2:
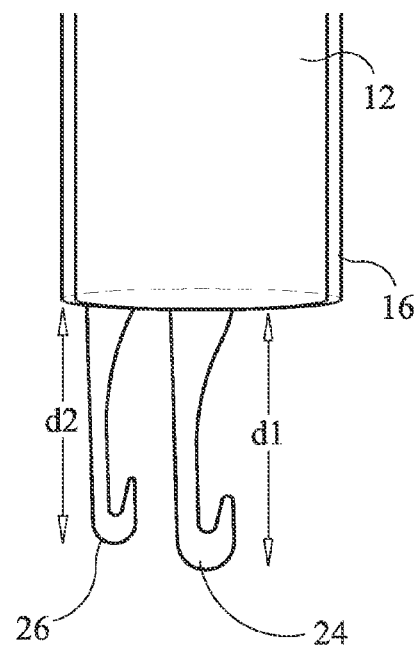
FIG. 2 is a side view of components of the system shown in FIG. 1.
Figure 3:
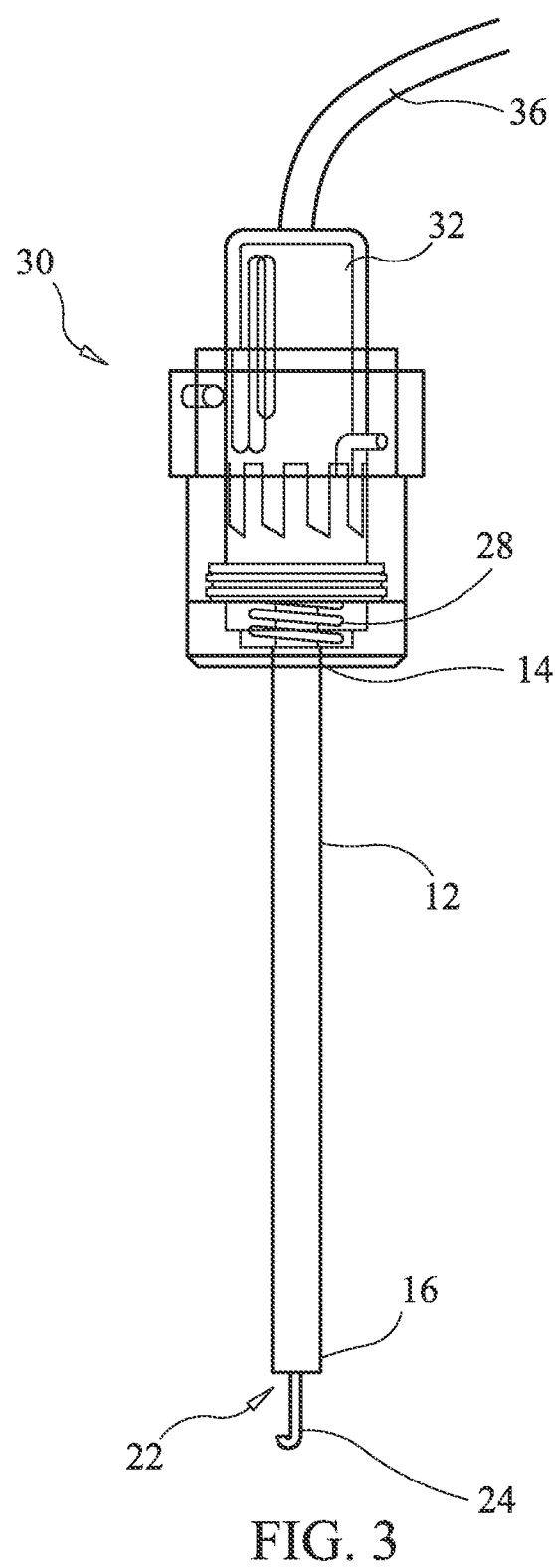
FIG. 3 is a perspective view, with partial cross section, of one embodiment of a surgical system in accordance with the principles of the present disclosure.

The following discussion includes a description of a system for performing a surgical procedure and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-3, there are illustrated components of the system for performing a surgical procedure in accordance with the principles of the present disclosure.

As shown in FIGS. 1-3, system 10 includes an elongated shaft, such as, for example, a cannula 12. Cannula 12 extends between a proximal end 14 and a distal end 16. Cannula 12 includes an outer surface 18 and an inner surface 20. Inner surface 20 defines a passageway 22. Passageway 22 extends the entire length of cannula 12 and has a cylindrical cross sectional configuration having a uniform diameter along the length of passageway 22. In some embodiments, passageway 22 may have alternate cross section configurations, such as, for example, oval, oblong, triangular, square, hexagonal, polygonal, irregular, uniform, non-uniform and/or tapered.

A first cutting element, such as, for example, a hook 24 extends through passageway 22 and extends out distal end 16. Hooke 24 can be an anchor hook or a suture hook, or any other type of cutting device suitable for the surgical procedure. As shown in FIG. 2, hook 24 is centrally disposed within passageway 22 and extends a distance d1 from distal end 16. Hook 24 is stationary within passageway 22 and remains in a fixed position during the surgical procedure so as to contact tissue. Hook 24 includes an outer surface that may be configured to enhance engagement with tissue, such as, for example, rough, arcuate, undulating, dimpled and/or textured, according to the requirements of a particular application. Hook 24 is configured to pull on the ligamentum flavum and dissect tissue.

As shown in FIG. 2, a second cutting element, such as, for example, an orbiting hook 26. Hook 26 extends through passageway 22 and extends from distal end 16. Hook 26 is configured for retractable extension beyond distal end 16 so as to contact tissue. Hook 26 includes an outer surface that may be configured to enhance engagement with tissue, such as, for example, rough, arcuate, undulating, dimpled and/or textured, according to the requirements of a particular application.

Hook 26 is resiliently biased, such as, for example, with a spring 28. A deployment mechanism 30 is configured to house spring 28. Mechanism 30 includes a cap 32 and an actuator, such as, for example, a button 34 configured to actuate hook 26 incrementally. Cap 32 is disposed with proximal end 14 of cannula 12. Button 34 is disposed with cap 32 and is engaged with spring 28 to translate hook 26 distally from distal end 16. Hook 26 travels a distance d2 that is less than distance d1. Deployment mechanism 30 can be calibrated such that hook 26 can translate distance d2 in one push of button 34 or hook 26 can translate distance d2 with at least two pushes of button 34. Hook 26 is configured to evacuate tissue into the cannula. In one embodiment, hook 26 extends out of distal end 16 in a straight path. In one embodiment, hook 26 can extend out of distal end 16 and circle around hook 24 as with each actuation of button 34.

In one embodiment, cannula 12 can be configured to engage a vacuum 36, as shown in FIG. 3, to suction the resected nerve and/or soft tissue. Alternatively, an additional channel is possible for delivering fluid to the surgical site. At its proximate end, cannula 12 can be operatively connected to vacuum 36 for providing suction to resected nerve and/or tissue. Any suitable aspirator, cylindrical or otherwise, or other mechanism that creates vacuum upon the movement of an actuating member thereof, may be utilized as a vacuum source. Vacuum 36 can be in fluid communication with passageway 22 for providing suction to remove cut nerve and/or soft tissue.

In some embodiments, cannula 12 and/or hooks, 24, 26 include one or a plurality of marker bands (not shown) comprising a radiopaque material. In one embodiment, the polymeric material is polyether block amide. In some embodiments, the highly radiopaque material incorporated into the polymeric material is barium sulfate, bismuth subcarbonate, tungsten, or a combination thereof. In some embodiments, hook 24 and/or hook 25 can include other dissection mechanisms, such as, for example, pinchers, knives, blades and/or electrodes emitting a cutting radio frequency.

In assembly, operation and use, system 10 is employed with a surgical procedure, such as, for a treatment of a hypertrophied ligamentum flavum. It is contemplated that one or all of the components of system 10 can be delivered or implanted as a pre-assembled device or can be assembled in situ. System 10 may be completely or partially revised, removed or replaced. It is envisioned that system 10 may also be used to treat other affected portions of the patient, such as, for example, a calcaneus bone, bones of the feet or hands, bones of the spine, bones of the arms and legs, etc.

In use, to a hypertrophied ligamentum flavum, the medical practitioner obtains access to a surgical site including in any appropriate manner, such as through the skin, or through an incision and retraction of tissues. In one embodiment, a drill is employed to remove bone tissue to provide access to a repair site. It is envisioned that system 10 can be used in any existing surgical method or technique including open surgery, mini-open surgery, minimally invasive surgery and percutaneous surgical implantation, whereby the fractured or injured bone is accessed through a mini-incision or sleeve that provides a protected passageway to the area. Once access to the surgical site is obtained, the particular surgical procedure can be performed for treating the injury or disorder. The configuration and dimension of system 10 is determined according to the configuration, dimension and location of a selected section of nerves and the requirements of a particular application.

An incision is made in the body of a patient and a cutting instrument (not shown) creates a surgical pathway for implantation of components of system 10. This may include the use of a cannula or other device. A preparation instrument (not shown) can be employed to prepare tissue surfaces, as well as for aspiration and irrigation of a surgical region according to the requirements of a particular surgical application.

Figure 4:
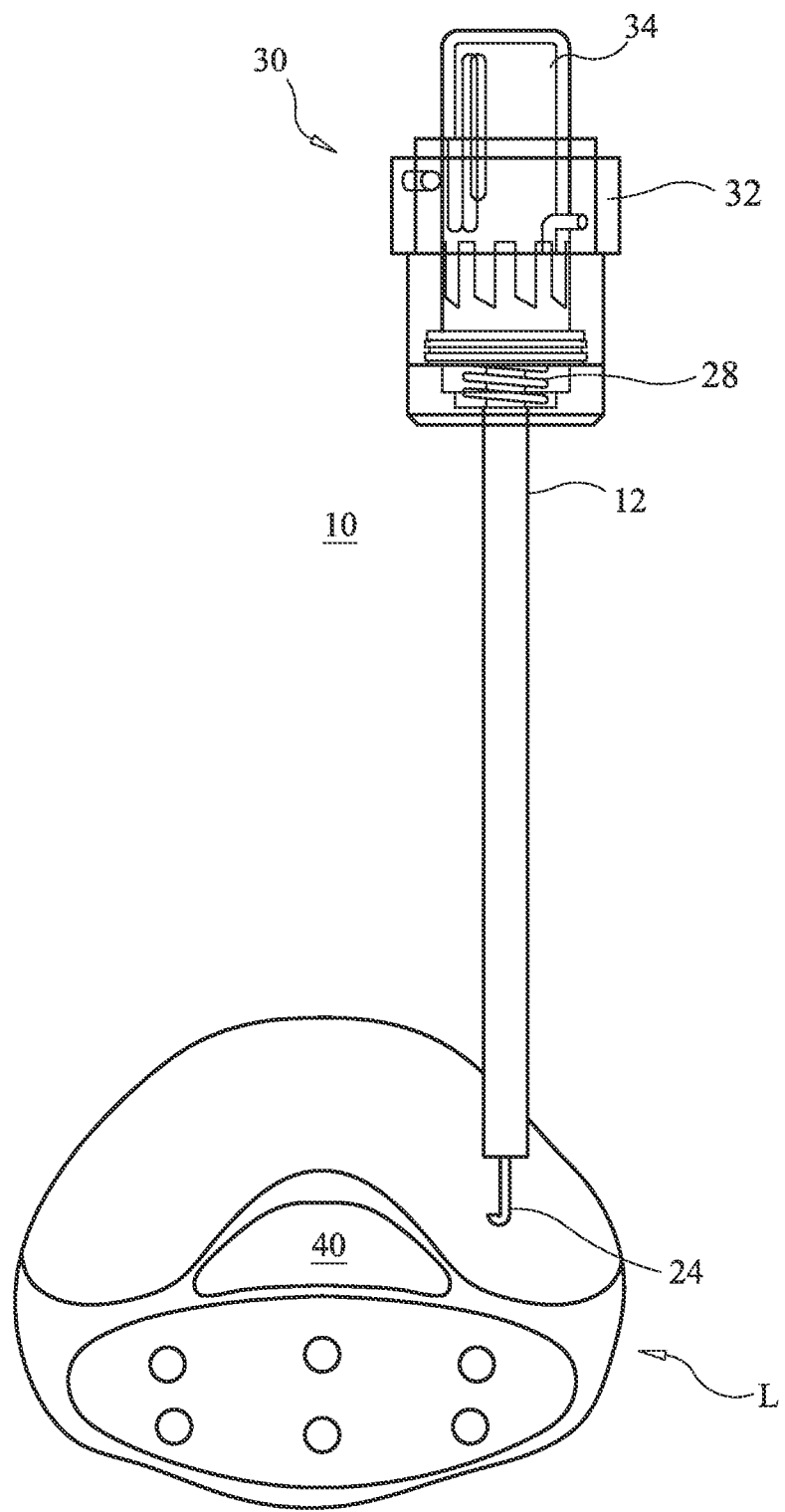
FIG. 4 is a side view of components of the system shown in FIG. 1 disposed with tissue.
Figure 5:
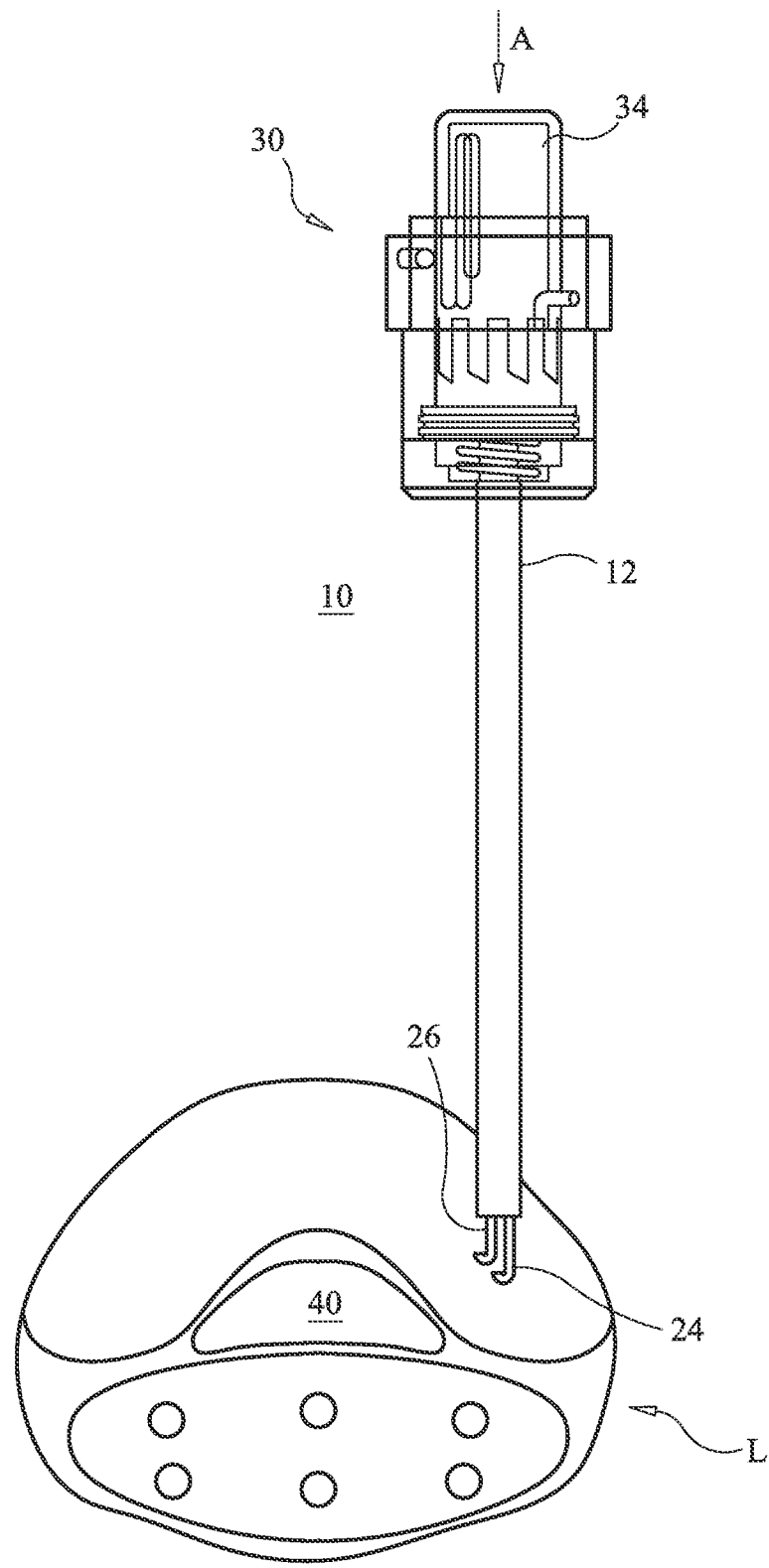
FIG. 5 is a side view of components of the system shown in FIG. 1 disposed with tissue.

As shown in FIGS. 4 and 5, device 10 is inserted into the surgical site of the ligamentum flavum L and manipulated such that hook 24 is in a position to pull on ligamentum flavum L and dissect tissue. The deployment mechanism 30 is actuated by pressing button 32 in the direction indicated by arrow A in FIG. 5. Actuation of deployment mechanism 30 causes hook 26 to extend past distal end 16. As shown in FIG. 2, hook 26 translates a distance d2 being less than the distance d1 that hook 24 extends past distal end 16. Hook 26 evacuates tissue and upon retraction back into cannula 12 pulls tissue into cannula 12. As shown in FIG. 3, a vacuum 36 can be attached to suction removed tissue such the cannula 12 is clear for additional dissection and evacuation of tissue.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The embodiments above can also be modified so that some features of one embodiment are used with the features of another embodiment. One skilled in the art may find variations of these preferred embodiments, which, nevertheless, fall within the spirit of the present invention, whose scope is defined by the claims set forth below.

What is claimed is:

1. A cutting device comprising:
    an elongated shaft extending between a proximal end and a distal end, the elongated shaft including an inner surface defining a passageway extending at least partially through the elongated shaft;
    a first cutting element disposed at least partially within the passageway and extending from the distal end of the elongated shaft so as to contact tissue;
    a second cutting element disposed at least partially within the passageway and extending from the distal end of the elongated shaft and configured for retractable extension beyond the distal end of the elongated shaft so as to contact tissue; and
    a deployment mechanism disposed within the proximal end of the elongated shaft and configured to engage the second cutting element wherein, upon actuation, the deployment mechanism is configured to circle the second cutting element around the first cutting element.

2. A cutting device as recited in claim 1, wherein the first cutting element is centrally located within the passageway of the elongated shaft and extends a distance from the distal end of the elongated shaft.

3. A cutting device as recited in claim 2, wherein the second cutting element is configured to extend a distance less than the distance of the first cutting element.

4. A cutting device as recited in claim 1, wherein the first cutting element is stationary within the passageway of the elongated shaft.

5. A cutting device as recited in claim 1, wherein the second cutting element is resiliently biased with the deployment mechanism such that the second cutting element extends out of the passageway so as to contact and cut tissue.

6. A cutting device as recited in claim 1, wherein the second cutting element is spring loaded with the deployment mechanism such that the cutting element extends out of the passageway so as to contact and cut tissue.

7. A cutting device as recited in claim 1, wherein the deployment mechanism includes a button to incrementally actuate the second cutting element.

8. A cutting device as recited in claim 1, wherein the first cutting element comprises an anchor hook.

9. A cutting device as recited in claim 1, wherein the first cutting element comprises a suture anchor.

10. A cutting device as recited in claim 1, wherein the elongated shaft further includes an attachment to a vacuum to produce suction so as to remove tissue.

11. A cutting device comprising:
a cannula extending between a proximal end, and a distal end, the cannula including an inner surface defining a passageway extending at least partially through the cannula;
a stationary anchor hook disposed at least partially within the passageway and extending from the distal end of the cannula so as to contact tissue;
an orbital hook disposed at least partially within the passageway and extending from the distal end of the cannula and configured for retractable extension beyond the distal end of the cannula so as to contact tissue; and
a deployment mechanism disposed within the proximal end of the cannula and configured to engage the orbital hook, wherein, upon actuation, the deployment mechanism is configured to circle the orbital hook around the stations anchor.

12. A cutting device as recited in claim 11, wherein the stationary anchor hook is centrally located within the passageway of the cannula and extends a distance from the distal end of the cannula.

13. A cutting device as recited in claim 11, wherein the orbital hook is resiliently biased with the deployment mechanism such that the orbital hook extends out of the passageway so as to contact and cut tissue.

14. A cutting device as recited in claim 11, wherein the orbital hook is spring loaded with the deployment mechanism such that the orbital hook extends out of the passageway so as to contact and cut tissue.

15. A cutting device as recited in claim 11, wherein the deployment mechanism includes a button to incrementally actuate the orbital hook.

16. A cutting device as recited in claim 11, wherein the orbital hook is configured to extend a distance less than the distance of the anchor hook.

17. A cutting device as recited in claim 11, wherein the cannula further includes an attachment to a vacuum to produce suction so as to remove tissue.

* * * * *